(12) United States Patent
Kenderian et al.

(10) Patent No.: US 6,945,114 B2
(45) Date of Patent: Sep. 20, 2005

(54) LASER-AIR, HYBRID, ULTRASONIC TESTING OF RAILROAD TRACKS

(75) Inventors: Shant Kenderian, Baltimore, MD (US); B. Boro Djordjevic, Severna Park, MD (US); Robert E. Green, Jr., Towson, MD (US); Donatella Cerniglia, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 10/449,655

(22) Filed: May 30, 2003

(65) Prior Publication Data

US 2004/0003662 A1 Jan. 8, 2004

Related U.S. Application Data

(60) Provisional application No. 60/429,279, filed on Nov. 25, 2002.

(51) Int. Cl.$^7$ .......................... G01N 29/10; G01N 29/24
(52) U.S. Cl. .............................. 73/643; 73/655; 73/656; 73/657
(58) Field of Search .......................... 73/579, 587, 597, 73/598, 599, 600, 643, 653, 655, 656, 657

(56) References Cited

U.S. PATENT DOCUMENTS

| | | | |
|---|---|---|---|
| 4,004,455 A | | 1/1977 | McKee ........................ 73/67.9 |
| 4,144,767 A | * | 3/1979 | Kaule et al. .................... 73/643 |
| 4,174,636 A | | 11/1979 | Pagano ......................... 73/636 |
| 4,235,112 A | | 11/1980 | Kaiser .......................... 73/634 |
| 4,512,197 A | * | 4/1985 | von Gutfeld et al. .......... 73/643 |
| 4,541,280 A | * | 9/1985 | Cielo et al. .................... 73/603 |
| 4,593,569 A | | 6/1986 | Joy .............................. 75/636 |
| 4,926,692 A | * | 5/1990 | Brokowski et al. ............ 73/597 |
| 5,257,544 A | * | 11/1993 | Khuri-Yakub et al. ........ 73/579 |
| 5,419,196 A | | 5/1995 | Havria ......................... 73/636 |
| 5,505,090 A | | 4/1996 | Webster ........................ 73/657 |
| 5,574,224 A | | 11/1996 | Jaeggi .......................... 73/636 |
| 5,636,026 A | | 6/1997 | Mian et al. ................... 356/376 |
| 5,698,787 A | | 12/1997 | Parzuchowski et al. ....... 73/643 |
| 5,801,312 A | | 9/1998 | Lorraine et al. .............. 73/602 |
| 5,824,908 A | | 10/1998 | Schindel et al. .............. 73/632 |
| 5,970,438 A | | 10/1999 | Clark et al. .................. 702/184 |
| 6,041,020 A | | 3/2000 | Caron ......................... 367/149 |
| 6,055,862 A | | 5/2000 | Martens ........................ 73/632 |
| 6,324,912 B1 | | 12/2001 | Wooh ........................... 73/629 |
| 6,335,943 B1 | | 1/2002 | Lorraine et al. .............. 372/28 |
| 6,360,609 B1 | * | 3/2002 | Wooh ........................... 73/602 |
| 6,378,387 B1 | | 4/2002 | Froom ........................ 73/865.8 |
| 2002/0108445 A1 | * | 8/2002 | Wooh ........................... 73/643 |

OTHER PUBLICATIONS

Kenderian, Djordjevic and Green, "Laser–Based and Air Coupled Ultrasound as Noncontact and Remote Techniques for Testing Railroad Tracks," *Materials Evaluation*, vol. 60(1), Jan. 2002, pp. 65–70.

(Continued)

*Primary Examiner*—Hezron Williams
*Assistant Examiner*—Rose M. Miller
(74) *Attorney, Agent, or Firm*—Larry J. Guffey

(57) ABSTRACT

Formed Laser Sources (FLS) using pulsed laser light for generation of ultrasonic stress waves are combined with air-coupled detection of ultrasound to provide for the hybrid non-contact, dynamic and remote ultrasonic testing of structural materials, especially railroad tracks. Using this hybrid technique, multimode and controlled frequency and wavefront surface acoustic waves, plate waves, guided waves, and bulk waves are generated to propagate on and within the rail tracks. The non-contact, remote nature of this methodology enables high-speed, fill access inspections of rail tracks. The flexibility and remote nature of this methodology makes possible the detection of critical cracks that are not easy, or impossible to detect, with current inspection techniques available to the railroad industry.

17 Claims, 10 Drawing Sheets

OTHER PUBLICATIONS

Kenderian, Djordjevic and Green, "Point and Line Source Laser Generation of Ultrasound for Inspection of Internal and Surface Flaws in Rail and Structural Materials," *Research in Nondestructive Evaluation*, vol. 13(4), Dec. 2001, pp. 189–200.

Kenderian and Djordjevic, "Narrowband Laser–Generated Surface Acoustic Waves Using A Formed Source In The Ablative Regime," *Journal of Acoustical Society of America*, to be published, Spring 2003.

Di Scalea, Kenderian & Green, Non–Contact Ultrasonic Inspection of Railroad Tracks, 45th International SAMPE Symposium, San Diego, CA, May 21–25, 2000.

Kenderian, Djordjevic and Green, Laser–Air Hybrid Ultrasonic Technique for the Inspection of Verical Cracks in Rails, 11th Inter. Symp. Nondestr. Char. Mater.—Berlin, Germany, Jun. 24–28,2002.

Cerniglia, Kenderian, Djordjevic, Garcia & Morgan, "Laser and Air–Coupled Transducer For Non–contact Ultrasonic Inspection In the Railroad Industry," AIPnD Conf., Spring 2003.

Kautz, "noncontact Determination of Antisymmetric Plarte Wave Velocity In Ceramic Matrix Composite," *Res. Nondestr. Eval.*, (1997) pp. 137–146.

Baldwin, Berndt & Ehrlich, "narrowband Laser Generaation/Air–Coupled Detection: UltrasonicSystem For On–line Process Control of Composites," "Ultrasonics," 37, pp. 329–334 (1999).

* cited by examiner

ULTRASONIC SIGNAL GENERATING MECHANISMS
INCLUDING THERMO-ELASTIC, ABLATIVE AND/OR SURFACE
WETTING AIDED GENERATION PROCESSES

POINT OR OPTIMIZED CIRCULAR AREA LASER SOURCE

LINE OR OPTIMIZED RECTANGULAR AREA LASER SOURCE

LINE ARRAY OR OPTIMIZED RECTANGULAR AREA ARRAY LASER SOURCE

LASER-AIR, HYBRID, ULTRASONIC TESTING OF RAILROAD TRACKS

CROSS-REFERENCE TO RELATED APPLICATION

This application claims the benefit of U.S. Provisional Patent Application No. 60/429,279, filed Nov. 25, 2002 by Shant Kenderian, B. Boro Djordjevic, Robert E. Green, Jr. and Donatella Cerniglia.

BACKGROUND OF THE INVENTION

1. Field of the Invention

This invention relates to non-contact, remote ultrasonic testing of railroad tracks. More particularly, Formed Laser Sources (FLS) using pulsed laser light for generation of ultrasonic stress waves are combined with air-coupled detection of ultrasound in a Laser-Air Hybrid Ultrasonic (LAHU) approach to non-contact, remote testing of railroad track.

2. Description of the Related Art

Maintenance of railroad rails is one of the greatest problems facing the transportation industry today. In one four-month period in 1998, a major railroad company experienced ten derailments due to broken rails at an expense of over $1.3 million. In its Newsletter, in September of 2000, the Texas Research Institute estimated that every ninety minutes a derailment, an accident, or any other rail related incident takes place in the US.

Despite the fact that a variety of inspection techniques have been used since the very early days of the introduction of railway, none of them is satisfactory for detection of many possible defects. The earliest of these methods, visual inspection, is obviously too slow and incapable of detecting internal defects in the rail. Furthermore, many defects on the surface of the rail are missed by the visual inspection method because of surface coverings of dirt, grease or other foreign matter.

The magnetic induction method, dating back to 1928, suffers from "liftoff" problems (magnetic field strength decreases with distance from surface of rail). It can only be used to identify surface breaking cracks.

The most current method, dating back to 1949, uses contact ultrasonic transducer sleds or piezoelectric ultrasonic transducers in a test car's rolling rubber wheels. These are filled with water or oil and in constant contact with the railroad track. These ultrasonic methods can detect both surface and internal cracks only when they are in favorable positions and orientations. They are not very effective in detecting Transverse Detail Defects (TDD), Vertical Split Heads (VSH), and rail base cracks. These three cracks are very critical and are the main cause of derailments.

Both the magnetic induction and ultrasonic methods examine only the rail top surface because of obstacles regularly appearing along the sides of the rail which fasten the rails together. In addition, these methods are currently limited to low testing speeds of about 10–15 mph.

In the U.S., the Federal Railroad Administration rules require that any indication considered suspect by the test equipment on a test car are hand verified immediately. This leads to a stop-start test mode, which effectively reduces the overall test speed in any given workday.

A more recent, non-contact means for inspecting rail track is disclosed in U.S. Pat. No. 6,324,912. It discloses the use of acoustic transducers for both the generation and detection of ultrasound on railroad tracks. The disclosed method relies on Doppler shifted frequencies caused by the high-speed motion between the rail and the source of the ultrasonic wave. The technique is estimated to be limited to operating velocities of the source of the ultrasonic waves that are above 65 mph and has been demonstrated only on a smooth laboratory spinning wheel.

Other air-coupled ultrasonic generation techniques rely on the resonance modes associated with the different cross-sections of the rail. Up to four hundred measurements are collected and averaged in order to obtain a discernable signal. The technique imposes a static condition between the probes and test specimen in order to perform averaging calculations while retaining phase of the resonant frequency. In addition, ultrasonic source air-coupled transducers are sensitive to their position and orientation with respect to the surface of the specimen. They often impose test configurations that place the test probes in positions that compromise their safety. These configurations are generally rejected by the railroad industry.

Frequency control of laser generated acoustic signals has been previously accomplished by temporal or spatial modulation. However, such temporal modulation requires a very high repetition rate, which would then translate to lower laser pulse energy. The resulting acoustic signals are too weak for most industrial applications.

Spatial modulation has been accomplished through the use of shadow masks, diffraction gratings, corrugated lenticular arrays or other means. All of these techniques produce specific illumination patterns and have low efficiency in delivering the laser energy to a surface in which defects are sought to be detected.

These techniques differ from those of the present invention. In the present invention, a series of high energy lenses are shaped in order to maximize the delivery of the laser energy to the targeted surface and to allow flexibility in shaping the illuminated region to produce optimum ultrasonic signals for the desired flaw detection capabilities.

The present inventors' early experiments utilizing non-contact, ultrasonic techniques for the inspection of railroad tracks were initially disclosed in May 2000. See "Non-Contact Ultrasonic Inspection of Railroad Tracks," 45th International SAMPE Symposium, San Diego, Calif., May 21–25, 2000. The teachings and disclosure of this work is hereby incorporated by reference. The experimental techniques of this early work used laser beams focused to a point. These early techniques will be seen to differ significantly from those revealed herein.

The present inventors have also documented much of the work that is disclosed herein in the scientific literature. See "Laser-Based and Air Coupled Ultrasound as Noncontact and Remote Techniques for Testing Railroad Tracks," *Materials Evaluation*, vol. 60(1), January 2002, pp. 65–70; "Point and Line Source Laser Generation of Ultrasound for Inspection of Internal and Surface Flaws in Rail and Structural Materials," *Research in Nondestructive Evaluation*, vol. 13(4), December 2001, pp. 189–200, "Narrowband Laser-Generated Surface Acoustic Waves Using A Formed Source In The Ablative Regime," *Journal of Acoustical Society of America*, to be published, Spring 2003, "Laser-Based and Air Coupled Ultrasound as Noncontact and Remote Techniques for Testing Railroad Tracks," (Translated to Italian), *The Journal of the Italian Society of Nondestructive Testing Monitoring Diagnostics*, vol. 23(2), 2002, pp. 34–41, "Laser And Air-Coupled Transducer For Non-Contact Ultrasonic Inspection In The Railroad Industry (in Italian)," ENEA Trisaia Research Center (MT) Italy, *AIPnD (Italian Society for Nondestructive Testing)*, To-Be Published 2003, "Laser- Air Hybrid Ultrasonic Technique for the Inspection of Rail Steel," 11$^{th}$ *International Symposium on Nondestructive Characterization of Materials*, Berlin, Germany. Jun. 24–28, 2002, (in publication), and "Sensitivity of Point And Line Source Laser Generated Acoustic Wave To Surface Flaws," *IEEE Transactions on Ultrasonics Ferroelectrics and Frequency Control*, To Be Published 2003. The teachings and disclosure of these works are hereby incorporated by reference.

With the rising cost of transportation and increasing number of drivers on the road, the use of passenger and cargo trains is becoming more attractive. However, before increasing the speed and axle load on railroad tracks, faster and more reliable inspection methods ate still needed in order to prevent property damage and life-threatening injury.

3. Objects and Advantages

There has been summarized above, rather broadly, the prior art that is related to the present invention in order that the context of the present invention may be better understood and appreciated. In this regard, it is instructive to also consider the objects and advantages of the present invention.

It is an object of the present invention to provide an improved testing method for inspecting railroad tracks.

It is another object of the present invention to provide a non-contact and remote testing method that can detect hard to find surface breaking and internal cracks, vertical and traverse cracks and other material discontinuities in railroad tracks.

It is yet another object of the present invention to provide a testing method that enables one to generate and detect ultrasonic signals on the base of the rail, web of the rail and from the side of the rail while still keeping all instrumentation and equipment remote and non-contact above the top surface of the rail.

It is a further object of the present invention to provide a rail track testing method and apparatus that utilizes Formed Laser Sources (FLS) methodology to enable one to control the wavefront and frequency of the laser-generated acoustic signal so as to yield optimum interaction with and detection of rail defects such as cracks.

It is a still further object of the present invention to provide a rail track testing method and apparatus that utilizes Laser-Air Hybrid Ultrasonic (LAHU) techniques and FLS sources to detect various types of critical cracks that cause rail reliability problems and are difficult or impossible to detect via conventional means.

It is an object of the present invention to provide a rail track testing apparatus and method that enables inspection of the complete rail and successfully detect cracks and other defects at test speeds exceeding those currently available to the railroad industry.

These and other objects and advantages of the present invention will become readily apparent as the invention is better understood by reference to the accompanying summary, drawings and the detailed description that follows.

SUMMARY OF THE INVENTION

Recognizing the need for the development of improved methods for detecting flaws in rail tracks, the present invention is generally directed to satisfying the needs set forth above and overcoming the disadvantages identified with prior art devices and methods.

In accordance with the present invention, the foregoing need can be satisfied by providing a remote, non-contact flaw or defect detection system for detecting a flaw in a structural material that is surrounded by a gaseous or vacuum environment, with the system operating by distinguishing the propagation differences between various modes of ultrasonic stress waves generated in the structural material. Such a system includes: (1) a means for generating, in a non-contact manner in the structural material, various modes of ultrasonic stress waves having specified, controlled frequencies and wavefronts, (2) a means, located at a specified location in the surrounding environment and spaced from the structural material, for sensing from the structural material an acoustic signal that distinguishes the propagation of the various modes of ultrasonic stress waves in the material, and (3) a means, responsive to the sensed acoustic signal, for distinguishing the differences between the various modes of the ultrasonic stress waves so as to identify any flaw in the structural material.

In preferred embodiments, Formed Laser Sources (FLS) using pulsed laser light for generation of ultrasonic stress waves are combined with air-coupled, such as air-capacitance, transducers to provide for the non-contact, dynamic and remote ultrasonic testing of structural materials, especially railroad tracks.

Thus, there has been summarized above, rather broadly, the present invention in order that the detailed description that follows may be better understood and appreciated. There are, of course, additional features of the invention that will be described hereinafter and which will form the subject matter of the eventual claims to this invention.

DESCRIPTION OF THE PREFERRED EMBODIMENT

Figure 1A:
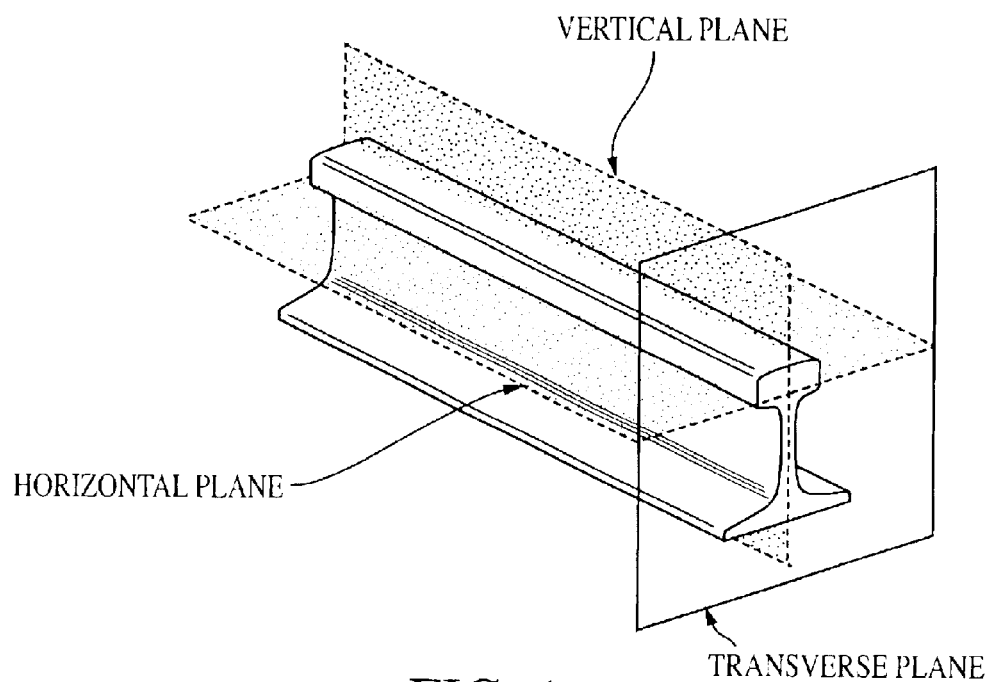
FIGS. 1(*a*)–(*b*) identify the vertical, horizontal and transverse planes of a railroad track, and its head, web and base portions.

Before explaining at least one embodiment of the present invention in detail, it is to be understood that the invention is not limited in its application to the details of construction and to the arrangements of the components set forth in the following description or illustrated in the drawings. The invention is capable of other embodiments and of being practiced and carried out in various ways. For example, the preferred embodiments disclosed herein are directed to detecting flaws in railroad tracks; however, it should be understood that these detection techniques are applicable to wide range of structural materials other than just railroad tracks. Also, it is to be understood that the phraseology and terminology employed herein are for the purpose of description and should not be regarded as limiting.

As previously mentioned, in-track rail inspections are currently performed using primarily a contact, ultrasonic method. Although this method has generally proven to be reliable, its results are far from perfect. In fact, train derailments caused by rail defects, which pass inspection, still occur.

Figure 1B:
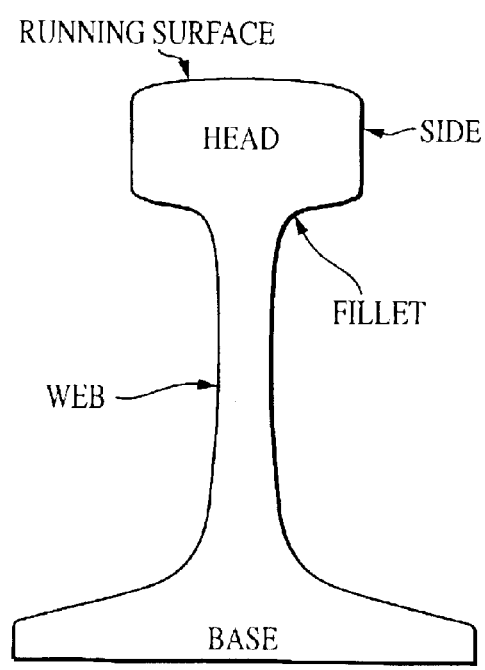

Several types of defects are commonly seen to exist in railroad tracks. These are classified according to their location and orientation in the rail, plus their nature. The ability to detect these defects may be affected by may factors, including: (1) rail surface conditions, (2) railhead geometry, (3) the orientation and geometry of the defect (e.g., surface and internal horizontal cracks versus transverse and vertical cracks), (4) electrical and/or mechanical noise introduced into the transducers being used, and (5) inadequate transducer-to-rail surface coupling. See FIGS. 1(a)–(b), which were taken from the "Rail Defect Manual" of Sperry Rail Service.

Some of these defects are especially worrisome as they cannot be detected using the current state-of-the-art contact, ultrasonic method. These include: vertical split heads (VSH), transverse defects, defective welds, and base defects.

There exist many reasons why these defects cannot be analyzed with the current contact, ultrasonic method. For example, VSH cracks have non-coplanar and nonlinear surfaces. Therefore, the ultrasonic energy directed to a VSH reflects in different directions from the defect and away from the point of incidence; thus, making the detection process a challenge with the rubber wheel of the contact, ultrasonic method.

In an effort to remedy this situation and improve railway safety, the Center for Nondestructive Evaluation (CNDE) at the Johns Hopkins University undertook a major research effort to identify and develop new and improved rail inspection technologies. This CNDE research has resulted in the invention of a Laser-Air Hybrid Ultrasonic (LAHU) approach with Formed Laser Sources (FLS) for the non-contact, remote testing of railroad track.

Figure 2:
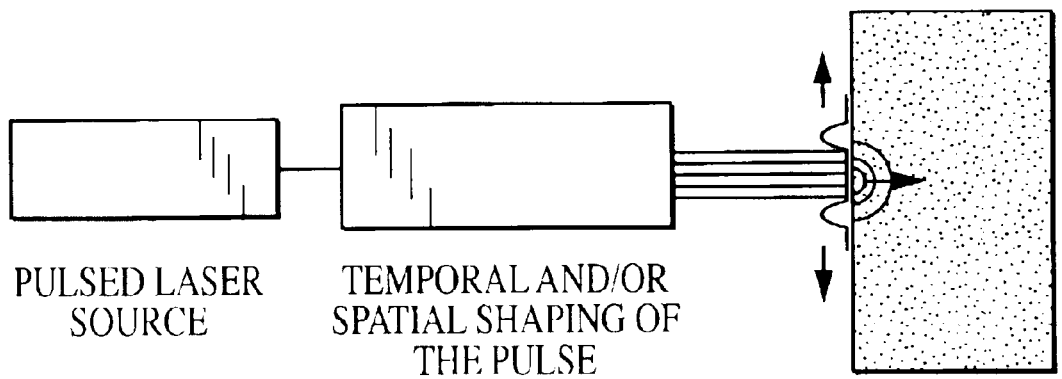
FIG. 2 illustrates FLS laser generation of controlled frequency and wavefront ultrasonic stress waves in a structural material.

Using this hybrid technique, multimode and controlled frequency and wavefront surface acoustic waves, guided waves, and bulk waves are generated to propagate on and within the rail tracks. See FIG. 2. The non-contact, remote nature of this methodology enables high-speed, full access inspections of rail tracks. By analog amplification, gating, digital signal capture, signal processing and digital data analysis and processing, such rail testing can be performed totally automated.

In a preferred embodiment, the present invention takes the form of a LAHU inspection apparatus that is mountable above a rail track, such as might be added onto a rail car or housed within a custom build rail car. To overcome the prior problems associated with obstacles in the proximity of a rail which limit the optimal placement of measurement transducers, the present invention uses air-coupled transducer arrays that capture the acoustical signals from different locations for analysis. As the car moves along the rail, the tracks are tested for defects such as cracks. Data is collected with a data capture and storage unit, whereupon the data is processed and decisions are made with regards the integrity of the rail track.

The prior art of the present inventors includes teachings for the inspection of railroad tracks using laser beams focused to a point. This differs from the techniques of the present invention which disclose how control over the frequency content of the laser-generated acoustic wave and the shape of the wave front is obtained by projecting the laser beam to form specified geometrical arrangements or illumination patterns.

Figure 3:
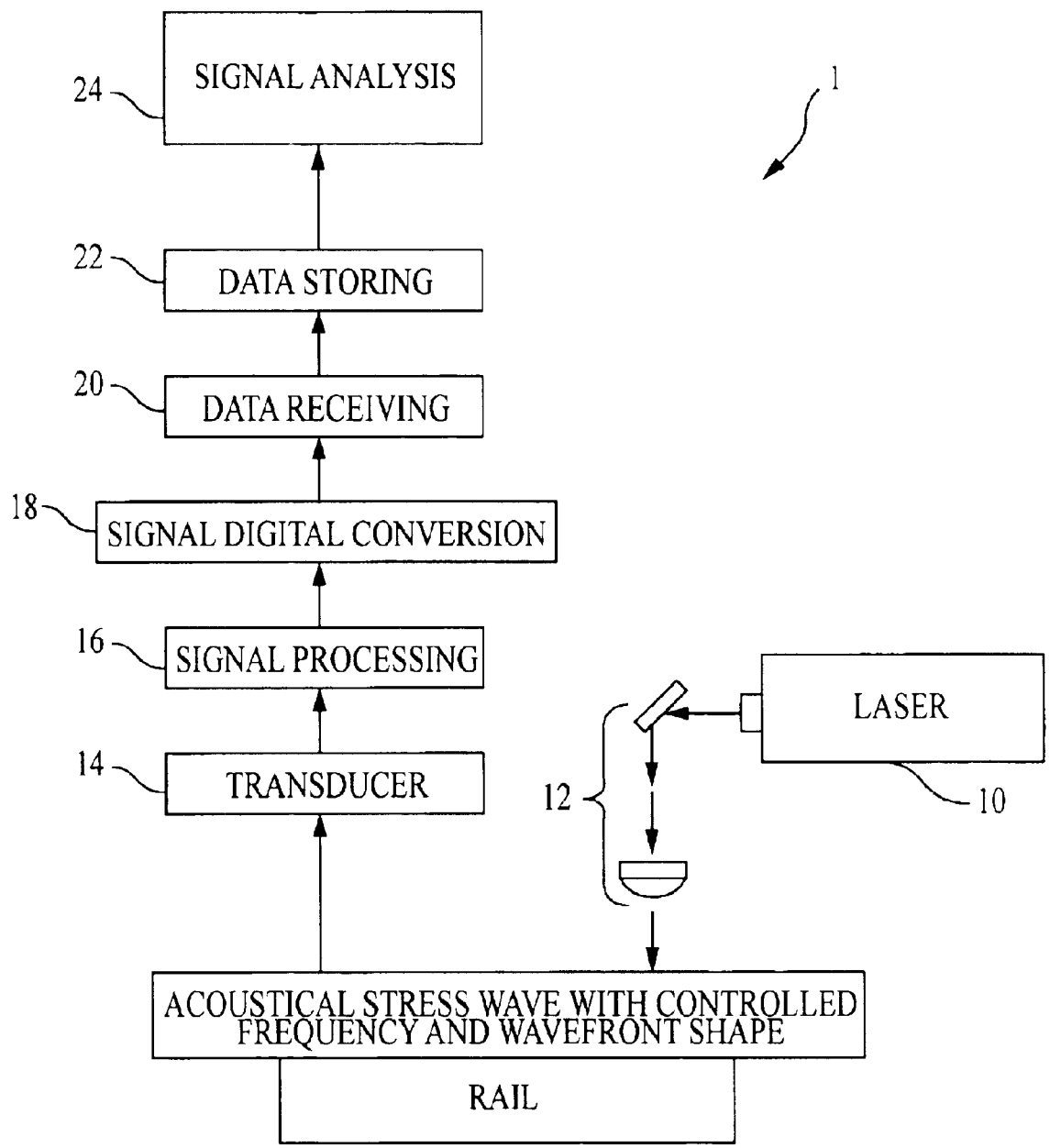
FIG. 3 shows a preferred embodiment for the configuration of the various components which comprise the system or apparatus of the present invention.

FIG. 3 illustrates schematically the arrangement of the elements of a preferred embodiment of the present invention for forming and controlling ultrasonic tests. It includes the following essential components: a light source 10 formed by mirror, lens and/or fiber optic assemblies 12, air-coupled sensors/transducers 14 combined with acoustical mirrors and waveguides in a single or array arrangements, signal processing 16, signal digital conversion 18, data receiving 20, data storing 22, signal analysis 24, processing, and record storing components.

A detailed description of the various aspects of a preferred embodiment for the remote, non-contact defect or flaw detection system 1 of the present invention follows:

Generation of Ultrasound

A short FLS pulse laser 10 (e.g., pulsed laser, Nd:YAG 1.06 $\mu$m, with 1–10 nanosecond pulse having maximum energy in the range of 100–10,000 mJ per pulse) is used to generate controlled frequency and wavefront ultrasound, including bulk, surface, plate and other guided mode acoustic waves. The laser light can be delivered to a rail surface through mirrors, fiber optic bundles, light pipes or combinations of optical components 12.

The laser light can operate in the thermoelastic, near-ablative, ablative or constrained acoustical source regimes. The constrained regime is attained by coating or wetting the surface of the rail with a layer of constraining compounds that are transparent to the laser wavelength. This includes water, oil, grease, graphite, glass, or transparent tape among a large number of other possible constraining layers. Operating the laser light in the ablative regime proves desirable because it provides strong ultrasonic signals which are easily detected with a capacitive air-coupled transducer.

The region illuminated by the laser light can be formed to a circle, rectangle, circle array, rectangle array or other more complex geometrical area configurations to allow control over the frequency, waveforms and other characteristics of the generated acoustic wave. Various light delivery shapes are generated through the use of shadow masks, lenticular arrays, optical fiber bundles or other means 12.

To enhance the signal sensitivity to a specific type of crack, a controlled frequency and directed wavefront ultrasonic signals are generated using formed laser pulses. Formed laser light pulses are created by spatially modifying the shape, repetition and spacing of a light illumination area on the rail or by temporal modulating the pulse for the desired frequency.

Figure 4A:
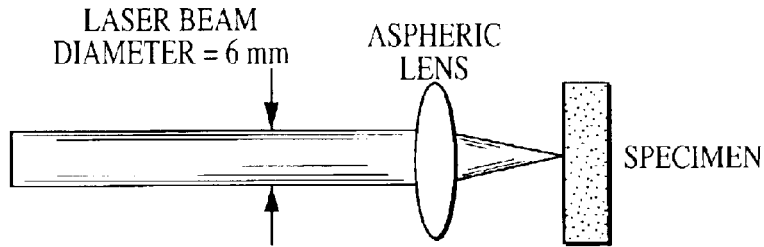
FIG. 4 illustrates the lens configurations for a laser generated: (a) point source, (b) line source, (c) line array source.
Figure 4B:
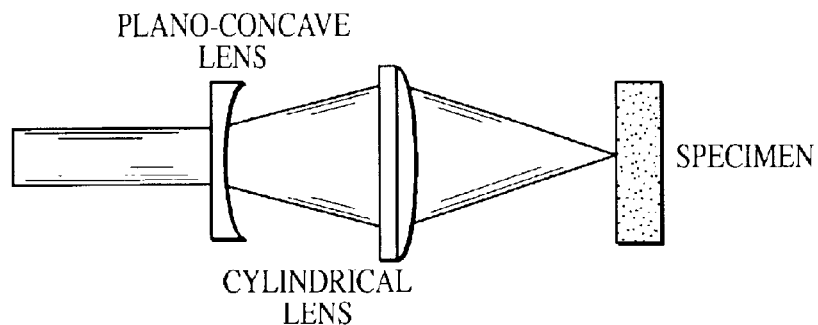
Figure 4C:
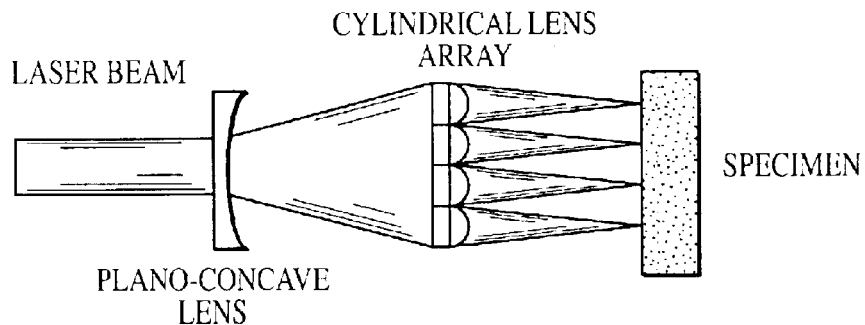

For example, inspection of internal defects in a rail head requires bulk waves which are generated by a point or optimized circular area laser source; whereas for the inspection of the rail base, guided waves are more appropriate and therefore the laser is focused into a line or optimized rectangular area source. See FIG. 4. The distance of lens assembly from the rail surface is determined by lens focal length.

Detection of Ultrasound

Figure 5A:
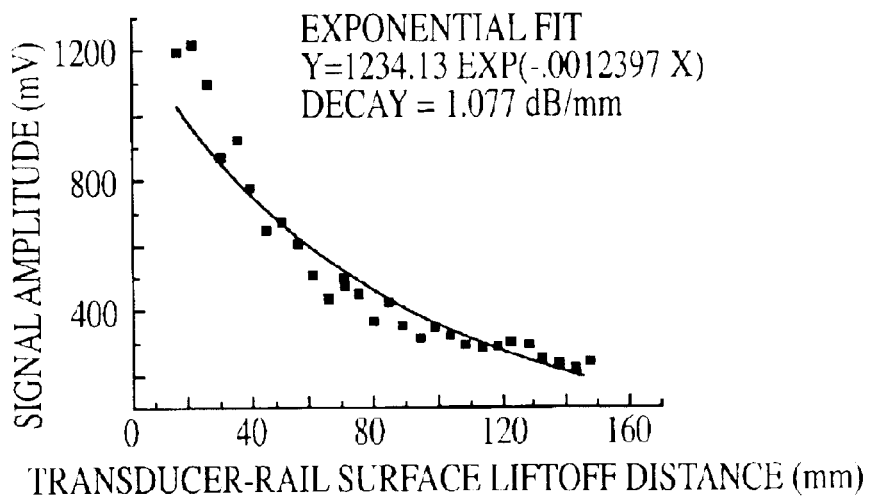
FIG. 5 shows the effect of the liftoff distance and angle of orientation on the signal strength of the capacitive air-coupled transducer detector of the present invention.
Figure 5B:
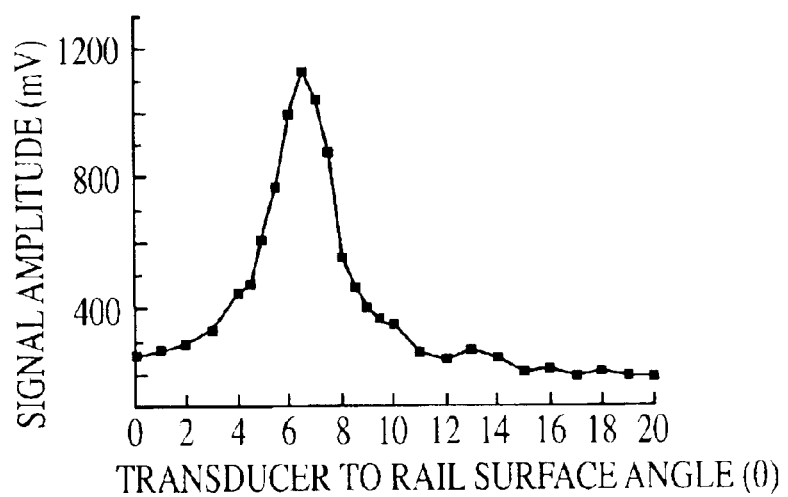
Figure 6:
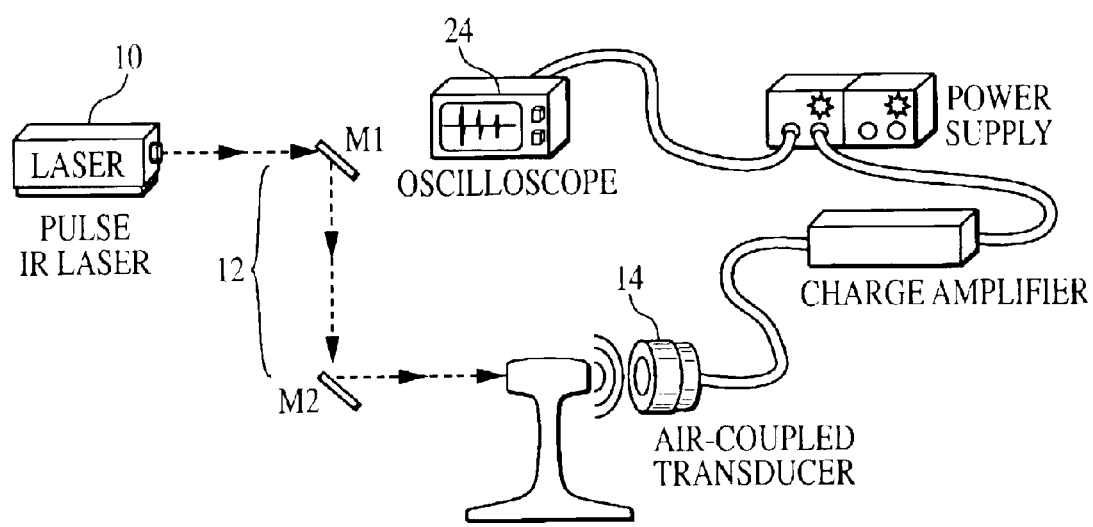
FIG. 6 illustrates the laser generation and air-coupled detection scheme in a preferred embodiment of the present invention.

For remote detection of ultrasound, capacitive air-coupled ultrasonic receivers 14 or gas ultrasonic wave detectors capable of detecting frequencies between 50 kHz and at least 3 MHz can be used. The effect of the liftoff distance and the angle of orientation of such a detector is shown in FIG. 5. They are seen to be capable of operating at liftoff distances exceeding 15 cm and to not be critically dependent on precise orientation or alignment. Air-coupled ultrasound signal detection can be performed via transducers that detect receive-signals by facing the surface of the rail track directly. See FIG. 6.

Figure 7:
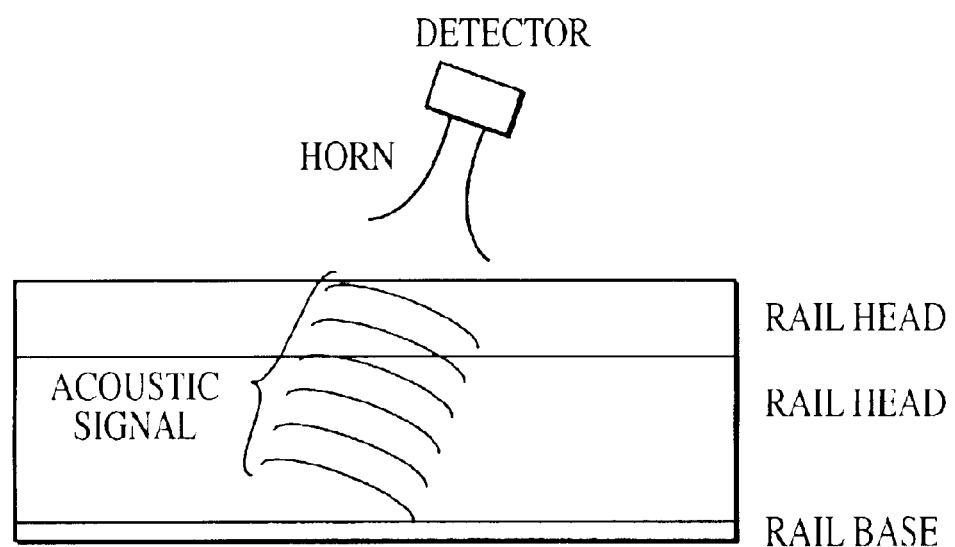
FIG. 7 illustrates how an acoustic signal can be collected and intensified using appropriate horns.

Acoustical mirrors and waveguides can be used to help in redirecting the sound fields to a detector. Waveguides enable capture of the signal at different angles from multiple locations and allow the receiving transducers to be placed at more flexible locations. Arrays of waveguides enable capture of ultrasonic signals from different locations. Horns can also be used to help in collecting, redirecting and intensifying the acoustic signal, see FIG. 7.

Data Capture and Processing

The data capture and processing 16 elements of the present invention includes signal analog amplification, signal gating, signal capture by digital means with multi-channel capability at resolutions as needed to process the signals. Ultrasonic signals are gated and analyzed in the time and frequency domains, classified via wavelet analysis or other feature and classification algorithms. Dedicated processors and software 24 are used to automatically characterize or assist in the characterization of existing defects in the rail tracks or other structural materials.

Methodology

Figure 8:
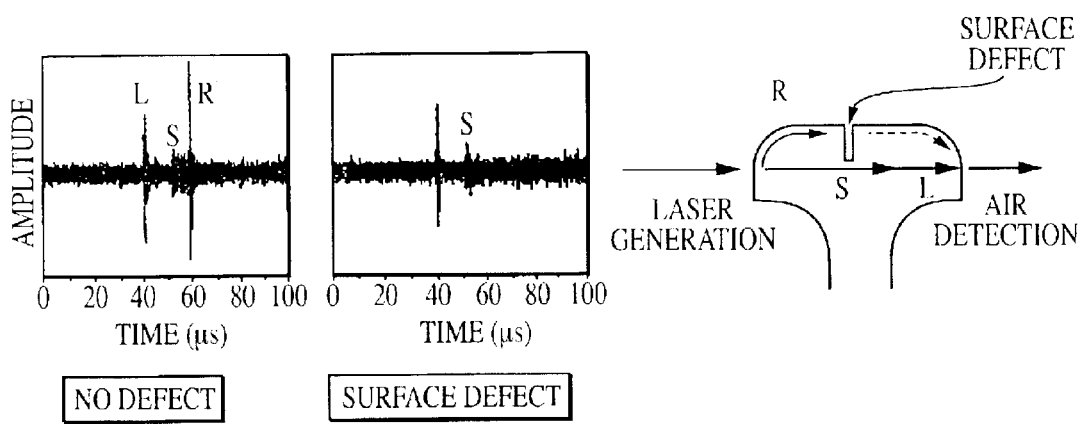
FIG. 8 demonstrates the phenomena of the generation with a single laser pulse of Longitudinal (L), Shear (S) and Rayleigh (R) waves that are used to detect a surface defect.
Figure 9:
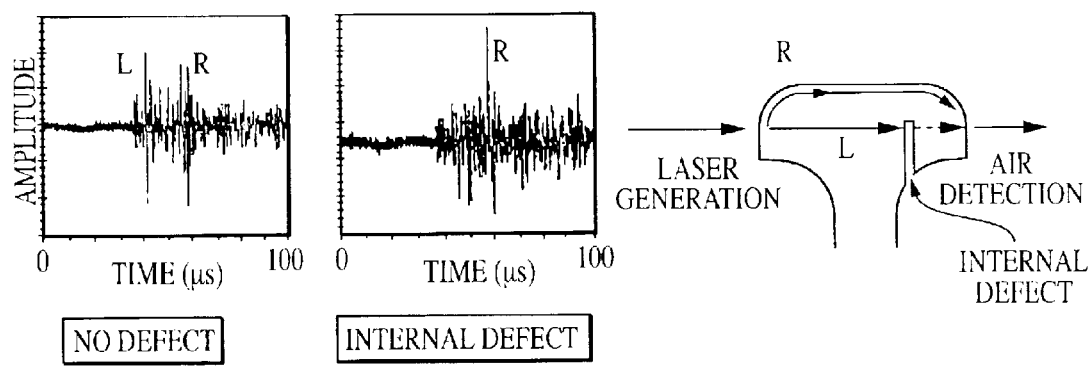
FIG. 9 demonstrates the phenomena of the generation with a single laser pulse of Longitudinal (L) and Rayleigh (R) waves that are used to detect an internal defect.

One of the unique characteristics of laser-based ultrasound is that with a single pulse, several modes of ultrasonic waves propagate in a material at the same time. Therefore, in a single test, longitudinal, shear and surface (Rayleigh) waves are generated simultaneously. FIGS. 8–9 demonstrate this phenomena where the amplitude of the signal received by a capacitive air-coupled transducer is plotted as a function of time. The times at which the respective waves are sensed by the transducer can be shown to be comparable to their predicted times of arrival at the transducer.

FIG. 8 shows that with a single pulse, a Longitudinal (L), Shear (S) and Rayleigh (R) wave are generated. The Rayleigh wave is interrupted by a surface-breaking crack, but the crack was not deep enough to intercept the Longitudinal and Shear bulk waves. The frequency content of these signals was observed to fall between 0.3 MHz and 2.0 MHz. This is due to a 0.3 MHz high pass filter used to minimize low frequency mechanical noise and the 2.0 MHz detection limit of the air-coupled transducer.

FIG. 9 shows that with a single pulse, Longitudinal and Rayleigh waves are generated. An internal defect in the rail is seen to not affect the Rayleigh wave, but to interrupt the Longitudinal wave.

Experimental Results For The Testing Of In-Track Rails

Preferred embodiments of the present invention were field evaluated for their ability to detect vertical split heads (VSH) and base defects in in-track rails.

Figure 10:
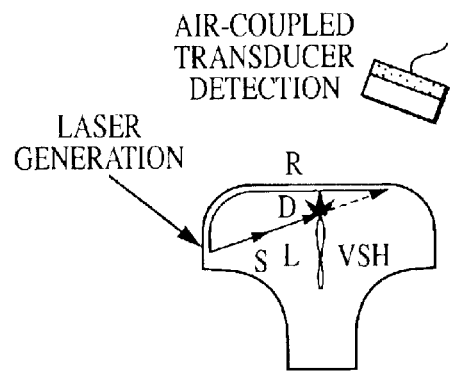
FIG. 10 illustrates the experimental setup used to inspect for VSH defects in in-track rails.

For the VSH defects, in-track inspections were performed with an air-coupled transducer located at least two inches above the railhead. See FIG. 10. The focused laser pointed directly to the field side of the rail head and generated Longitudinal and Shear waves in the rail and Rayleigh wave on the running surface of the railhead.

Figure 11:
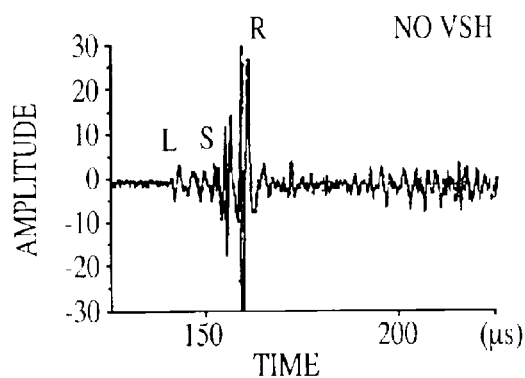
FIG. 11 illustrates the amplitude of the signal being received by the transducer of FIG. 10 as a function of time when no VSH defect is present in the rail; the focused laser pointed directly to the field side of the rail head is seen to generate Longitudinal and Shear waves in the rail and Rayleigh waves on the running surface of the railhead.
Figure 12:
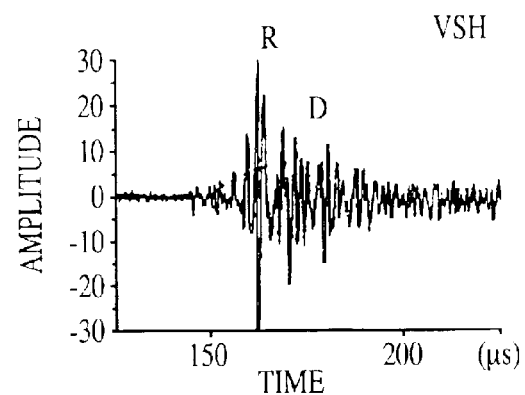
FIG. 12 illustrates the amplitude of the signal being received by the transducer of FIG. 10 as a function of time when a VSH defect is present in the rail; in the presence of a VSH defect, the Longitudinal and Shear waves are attenuated while the Rayleigh wave is not affected.

The waveform for the no-VSH defect condition is shown in FIG. 11. All the generated wave modes are clearly identifiable in the transducer's output. In the presence of a VSH defect, the Longitudinal and Shear waves are attenuated while the Rayleigh wave is not affected. See FIG. 12. Moreover, some diffraction (D) is seen to be created around the tip of the defect. Inclination of such a VSH defect in the cross-section of the rail was not seen to affect detection. Railhead tests for VSH defects were repeatable and 100% successful.

Figure 13:
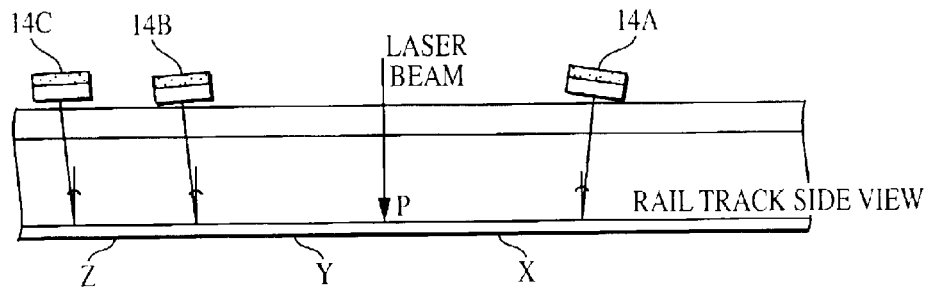
FIG. 13 illustrates the experimental setup used to inspect for base defects in in-track rails.

Rail base defects inspected in these experiments were through the base thickness, at the bottom and top base surface. The laser beam was focused into a line on the outer edge of the rail base. Each of the three transducers 14A, 14B, 14C were located as shown in FIG. 13 to detect the direct, reflected or transmitted surface wave depending on a crack's location (e.g., positions X, Y or Z). The orientation angle of each transducer was 6.5° with respect to the normal to the rail base surface.

Figures 14A, 14B, 14C:
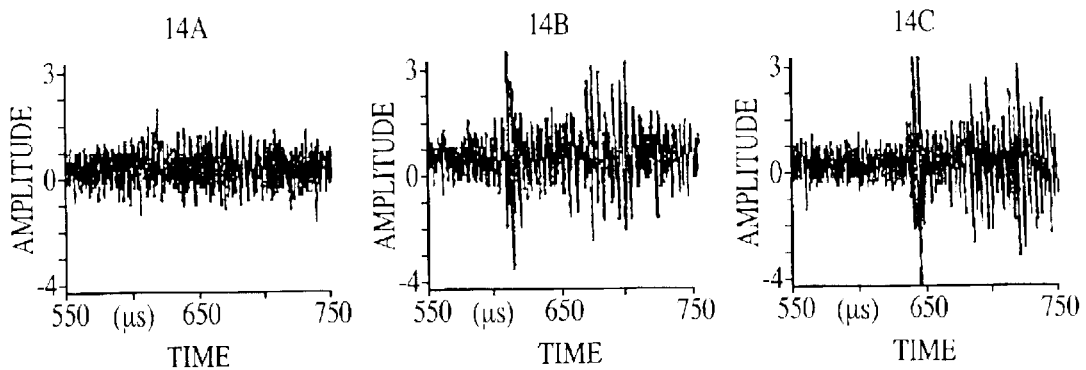
FIGS. 14(a)–(c) illustrates the amplitude of the signal being received by the transducers 14A, 14B and 14C of FIG. 13 as a function of time when a base defect is present at position X in the rail; the crack is seen to interrupt the Rayleigh wave such that it is not seen in the output of transducer 14A.
Figures 15A, 15B:
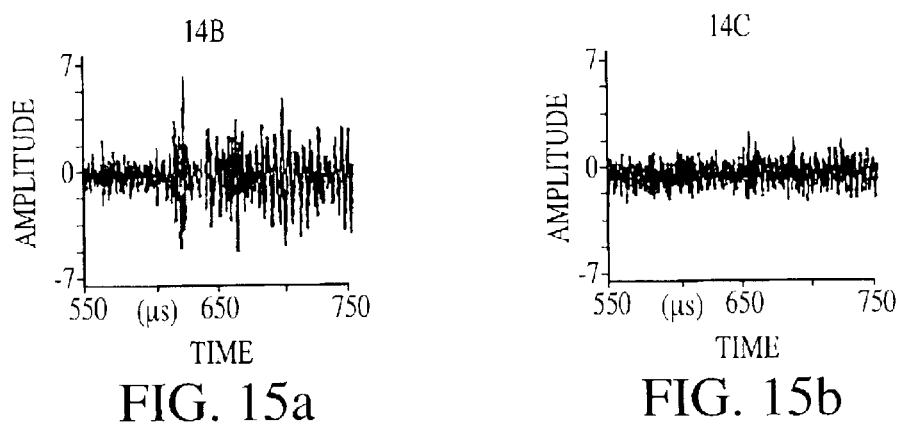
FIGS. 15(a)–(b) illustrates the amplitude of the signal being received by the transducers 14B and 14C of FIG. 13 as a function of time when a base defect is present at position Z in the rail; the crack is seen to interrupt the Rayleigh wave such that it is not seen in the output of transducer 14C.

Signal waveforms were analyzed for attenuation and the presence of reflected waves. For the cracks at the bottom surface of the rail base, reflected waves are not clearly seen. Signal waveforms acquired by transducers 14A, 14B and 14C in the presence of a bottom surface crack located between the generation point (P) and 14A (i.e., X) are shown in FIGS. 14(a)–(c), respectively. The crack is easily located by comparing the signals detected by transducers 14A and 14B and noting the attenuation seen in the output of transducer 14A. Similarly, a crack located between transducers 14B and 14C (i.e., Z) affects the signal detected by transducer 14C but not that detected by 14B, see FIGS. 15(a)–(b).

The present invention is seen to provide a new methodology, testing system and concept to enable non-contact and remote ultrasonic testing of railway track and related components. This non-contact remote testing is possible by the novel use of laser sound generation, coupled with guided ultrasonic stress waves and their evaluation using remote highly sensitive, air-coupled ultrasonic transducers.

The apparatus that enables such non-contact and remote testing of rail components can be arranged so that no optical, mechanical or sensor components are below the top of the rail line. The basic system can be adapted to different configurations by changing set-up geometry and by changing formed laser light patterns and controlling the stress wave signals in the rail. By changing wavefront, frequency and directivity of light generated stress waves, the ultrasonic tests are now controlled and the sensing apparatus achieves enhanced performance so as to enable it to detect specific type of rail defects.

With the present invention, it is now possible to test railway tracks from static and/or moving sensor array platforms in an automated and non-contact manner. These testing configurations eliminate the restriction of conventional contact transducer testing that is limited to the rail head top and cannot access below rail head level because of obstructions and component geometry restrictions that prevent direct coupling contact of ultrasonic transducers to the rail.

Combining a laser (light) formed impulse source with air coupled remote sensors, the test system performance of the present invention is enhanced beyond conventionally anticipated results. For one, there is no cross-talk or acoustical coupling between ultrasound generating and receiving components. Because the transduction is based on different physical mechanisms the two transducers do not interact acoustically.

With respect to the above description, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention. Furthermore, it should be noted that the methodology enclosed herein is suitable for the inspection of many structures or materials in general.

Therefore, the foregoing is considered as illustrative only of the principles of the present invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention as will later be set forth in the claims of the regular patent application that will be filed to protect the present invention.

We claim:

1. A remote, non-contact system for detecting a defect in a structural material that is surrounded by a gaseous or vacuum environment, said system comprising:
    a remote means, located at a first specified location in said environment and spaced from said structural material, for generating, in a non-contact manner in said structural material, modes of ultrasonic stress waves having a specified, controlled wavefront and frequencies,
    a non-contact means, located at a second specified location in said environment and spaced from said structural material, for sensing from said structural material an acoustic signal in said environment that distinguishes the propagation of said modes of ultrasonic stress waves in said structural material, and
    a means, responsive to said sensed acoustic signal, for distinguishing in said sensed signal the differences between said modes of said sensed ultrasonic stress waves so as to detect said defect in said structural materials,
    wherein said structural material is a metal in a complex-shaped form.

2. A defect detection system as recited in claim 1, wherein said controlled wavefront is chosen so as to yield said stress waves having frequencies that match the frequency sensing capabilities of said non-contact, sensing means.

3. A defect detection system as recited in claim 1, wherein said controlled frequency is chosen so as to yield said stress waves having frequencies that match the frequency sensing capabilities of said non-contact, sensing means.

4. A defect detection system as recited in claim 2, wherein said controlled frequency is chosen so as to yield said stress waves having frequencies that match the frequency sensing capabilities of said non-contact, sensing means.

5. A defect detection system as recited in claim 1, wherein said defect is of a specified type and said controlled wavefront and frequencies are chosen so as to enhance the sensitivity of said non-contact, sensing means to said specified type of defect.

6. A remote, non-contact method for detecting a defect in a structural material that is surrounded by a gaseous or vacuum environment, said method comprising the steps of:
    generating, in a non-contact manner in said structural material, modes of ultrasonic stress waves having a specified, controlled wavefront and frequencies,
    sensing from said structural material an acoustic signal in said environment that distinguishes the propagation of said modes of ultrasonic stress waves in said structural material, and
    distinguishing in said sensed signal the differences between said modes of said sensed ultrasonic stress waves so as to detect said defect,
    wherein said structural material is a metal in a complex-shaped form.

7. A defect detection method as recited in claim 6, wherein said controlled wavefront is chosen so as to yield said stress waves having frequencies that match the frequency sensing capabilities encountered in said sensing step.

8. A defect detection method as recited in claim 6, wherein said controlled frequency is chosen so as to yield said stress waves having frequencies that match the frequency sensing capabilities encountered in said sensing step.

9. A defect detection method as recited in claim 7, wherein said controlled frequency is chosen so as to yield said stress waves having frequencies that match the frequency sensing capabilities encountered in said sensing step.

10. A defect detection method as recited in claim 6, wherein said defect is of a specified type and said controlled wavefront and frequencies are chosen so as to enhance the signal sensitivity encountered in said sensing step to said specified type of defect.

11. A remote, non-contact system for detecting a defect in a structural material that is surrounded by a gaseous or vacuum environment, said system comprising:
    a pulsed, laser light source, located at a first specified location in said environment and spaced from said structural material, for generating in said structural material, modes of ultrasonic stress waves,
    a lens in the path of the light from said light source for focusing said light into a specified illumination pattern to generate a controlled ultrasonic wavefront,
    an air-coupled transducer, located at a second specified location in said environment and spaced from said structural member, for sensing from said structural material an acoustic signal in said environment that distinguishes the propagation of said modes of ultrasonic stress waves in said structural material, and
    a signal processor, responsive to said sensed acoustic signal, for distinguishing in said sensed signal the differences between said modes of said ultrasonic stress waves so as to detect said defect, wherein said structural material is a metal in a complex-shaped form.

12. A defect detection system as recited in claim 11, wherein said controlled wavefront is chosen so as to yield said stress waves having frequencies that match the frequency sensing capabilities of said transducer.

13. A defect detection system as recited in claim 11, wherein said pulsed laser is modulated so as to yield said stress waves having frequencies that match the frequency sensing capabilities of said transducer.

14. A defect detection system as recited in claim 12, wherein said pulsed laser is modulated so as to yield said stress waves having frequencies that match the frequency sensing capabilities of said transducer.

15. A defect detection system as recited in claim 11, wherein said defect is of a specified type and said controlled wavefront is chosen so as to enhance the sensitivity of said transducer to said specified type of defect.

16. A defect detection system as recited in claim 11, wherein said structural material is a railroad track and said defect is an internal defect in a rail head, said controlled wavefront is a circular area source.

17. A defect detection system as recited in claim 11, wherein said structural material is a railroad track and said defect is a surface defect in a rail base, said controlled wavefront is a rectangular area source.

* * * * *